United States Patent
Desenne et al.

(10) Patent No.: US 9,566,220 B2
(45) Date of Patent: Feb. 14, 2017

(54) COMPOSITION CONTAINING A VOLATILE LINEAR ALKANE AND A NONIONIC ASSOCIATIVE POLYMER, USEFUL FOR CONDITIONING THE HAIR

(71) Applicant: L'OREAL, Paris (FR)

(72) Inventors: Patricia Desenne, Pringy (FR); Claire Bourdin, Levallois Perret (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/683,345

(22) Filed: Apr. 10, 2015

(65) Prior Publication Data

US 2015/0216772 A1 Aug. 6, 2015

Related U.S. Application Data

(63) Continuation of application No. 12/977,204, filed on Dec. 23, 2010, now abandoned.

(60) Provisional application No. 61/296,489, filed on Jan. 20, 2010.

(30) Foreign Application Priority Data

Dec. 23, 2009 (FR) ...................................... 09 59481

(51) Int. Cl.
| | | |
|---|---|---|
| *A61K 8/73* | (2006.01) | |
| *A61K 8/86* | (2006.01) | |
| *A61K 8/31* | (2006.01) | |
| *A61K 8/81* | (2006.01) | |
| *A61Q 5/12* | (2006.01) | |
| *A61K 8/891* | (2006.01) | |

(52) U.S. Cl.
CPC . *A61K 8/31* (2013.01); *A61K 8/73* (2013.01); *A61K 8/732* (2013.01); *A61K 8/8152* (2013.01); *A61K 8/86* (2013.01); *A61K 8/891* (2013.01); *A61Q 5/12* (2013.01); *A61K 2800/30* (2013.01); *A61K 2800/548* (2013.01)

(58) Field of Classification Search
CPC .......... A61K 8/31; A61K 8/8152; A61K 8/86; A61K 8/732; A61K 8/73; A61K 8/891; A61Q 5/12

See application file for complete search history.

(56) References Cited

U.S. PATENT DOCUMENTS

| | | |
|---|---|---|
| 3,818,105 A | 6/1974 | Coopersmith et al. |
| 8,722,029 B2 | 5/2014 | Desenne et al. |
| 2010/0183536 A1 | 7/2010 | Ansmann et al. |
| 2011/0064681 A1 | 3/2011 | Wendel et al. |
| 2011/0150786 A1 | 6/2011 | Desenne et al. |
| 2011/0150809 A1 | 6/2011 | Desenne et al. |
| 2011/0150813 A1 | 6/2011 | Desenne et al. |
| 2011/0171153 A1 | 7/2011 | Desenne et al. |
| 2012/0003172 A1 | 1/2012 | Desenne et al. |
| 2012/0009138 A1 | 1/2012 | Desenne et al. |

FOREIGN PATENT DOCUMENTS

| | | | |
|---|---|---|---|
| DE | 10 2008 012 457 | 12/2008 | |
| EP | 1 464 320 | 10/2004 | |
| FR | 0 035 899 | 9/1981 | |
| FR | 2 926 981 | 8/2009 | |
| WO | WO 9531173 A1 * | 11/1995 | ............. A61K 8/891 |
| WO | WO 00/37041 | 6/2000 | |

OTHER PUBLICATIONS

Jones, C., "Multifunctional Synthetic Rheology Modifiers for Personal Care Formulations: More than Just Thickeners," Rohm and Haas Personal Care, May 1, 2005, pp. 1-23. XP007909943.

"Personal Care Compositions with Beneficial Properties", IP. Com. Journal, Inc. Com. Inc., West Henrietta, NY, US, Apr. 3, 2009. XP013130819 ISSN: 1533-0001. pp. 53-60.

* cited by examiner

*Primary Examiner* — Nannette Holloman
(74) *Attorney, Agent, or Firm* — Oblon, McClelland, Maier & Neustadt, L.L.P.

(57) ABSTRACT

The invention relates to compositions and their use for conditioning keratin fibers, in particular the hair. The composition contains in a cosmetically acceptable medium, one or more volatile linear alkanes, and one or more nonionic associative polymers.

10 Claims, No Drawings

COMPOSITION CONTAINING A VOLATILE LINEAR ALKANE AND A NONIONIC ASSOCIATIVE POLYMER, USEFUL FOR CONDITIONING THE HAIR

REFERENCE TO PRIOR APPLICATIONS

This application claims priority to U.S. provisional application Ser. No. 61/296,489, filed Jan. 20, 2010; and to French patent application 09 59481, filed Dec. 23, 2009, both incorporated herein by reference.

FIELD OF THE INVENTION

The present invention relates to the use of a cosmetic composition comprising, in a cosmetically acceptable medium, one or more volatile linear alkanes and one or more nonionic associative polymers, for conditioning keratin fibres, in particular the hair. The described composition also makes up a part of the invention.

BACKGROUND OF THE INVENTION

Many haircare products have been described in the prior art. The purpose of the corresponding compositions is to give the hair good cosmetic properties.

It is known practice to use volatile solvents in rinse-out or leave-in haircare products. These volatile solvents generally make it possible to modify the sensory feel of a hair product by giving it a light structure that is not tacky in the hand. They also give it slipperiness, which facilitates its spreading on the hair, and in particular on dry hair.

Furthermore, in compositions in aqueous emulsion form of oil-in-water type, which are in the form of more or less gelled creams, the addition of volatile solvents may also make it possible to dissolve silicone gums, which are otherwise difficult to introduce into compositions on account of their intrinsic viscosity.

However, such volatile solvents, in particular liquid fatty esters, hydrocarbon-based oils such as isododecane or isohexadecane, and silicone oils such as cyclomethicone, may especially give rise to problems in terms of a greasy feel, lack of sheen and stiff, hard hair.

Documents DE 10 2008 017 031 and WO 2007/068 371 moreover disclose antisun compositions comprising a mixture of volatile linear alkanes and a nonionic associative polymer of the vinylpyrrolidone copolymer type.

Thus, there is a need to provide cosmetic haircare compositions which can improve smoothing and sheen on wet hair, which transform the keratin fibre during the optional rinsing, which facilitate the passage of a brush during brushing, and which can improve the softness, smoothing, sheen, suppleness and lightness on dry hair.

DETAILED DESCRIPTION OF THE PREFERRED EMBODIMENTS

It has now been discovered, surprisingly, that the combination of one or more volatile linear alkanes and of one or more nonionic associative polymers can be used to solve the problems of the prior art and to afford the desired effects mentioned previously.

Thus, one subject of the invention is the use for conditioning keratin fibres, in particular the hair, of a cosmetic composition comprising, in a cosmetically acceptable medium, one or more volatile linear alkanes and one or more nonionic associative polymers. The composition also makes up a part of the invention.

The composition used according to the invention contains one or more volatile linear alkane(s). The term "one or more volatile linear alkane(s)" means, without preference, "one or more volatile linear alkane oil(s)".

A volatile linear alkane that is suitable for use in the invention is liquid at room temperature (about 25° C. and at atmospheric pressure (760 mmHg).

The term "volatile linear alkane that is suitable for use in the invention" means a cosmetic linear alkane that can evaporate on contact with the skin in less than one hour, at room temperature (25° C.) and atmospheric pressure (760 mmHg, i.e. 101 325 Pa), which is liquid at room temperature, especially having an evaporation rate ranging from 0.01 to 15 mg/cm$^2$/minute, at room temperature (25° C.) and atmospheric pressure (760 mmHg).

Preferably, the volatile linear alkane(s) that are suitable for use in the invention have an evaporation rate ranging from 0.01 to 3.5 mg/cm$^2$/minute, at room temperature (25° C.) and atmospheric pressure (760 mmHg).

Preferably, the volatile linear alkane(s) that are suitable for use in the invention have an evaporation rate ranging from 0.01 to 1.5 mg/cm$^2$/minute, at room temperature (25° C.) and atmospheric pressure (760 mmHg).

More preferably, the volatile linear alkane(s) that are suitable for use in the invention have an evaporation rate ranging from 0.01 to 0.8 mg/cm$^2$/minute, at room temperature (25° C.) and atmospheric pressure (760 mmHg).

Even more preferably, the volatile linear alkane(s) that are suitable for use in the invention have an evaporation rate ranging from 0.01 to 0.3 mg/cm$^2$/minute, at room temperature (25° C.) and atmospheric pressure (760 mmHg).

Even more preferably, the volatile linear alkane(s) that are suitable for use in the invention have an evaporation rate ranging from 0.01 to 0.12 mg/cm$^2$/minute, at room temperature (25° C.) and atmospheric pressure (760 mmHg).

The evaporation rate of a volatile alkane in accordance with the invention (and more generally of a volatile solvent) may especially be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ with regulated temperature (25° C.) and hygrometry (50% relative humidity).

The liquid is allowed to evaporate freely, without stirring it, while providing ventilation by means of a fan (Papst-Motoren, reference 8550 N, rotating at 2700 rpm) placed in a vertical position above the crystallizing dish containing the volatile hydrocarbon-based solvent, the blades being directed towards the crystallizing dish, 20 cm away from the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of the time (in minutes).

The evaporation rate is then calculated, which corresponds to the tangent to the origin of the curve obtained. The evaporation rates are expressed in mg of volatile solvent evaporated per unit surface area (cm$^2$) and per unit of time (minutes).

According to one preferred embodiment, the volatile linear alkane(s) that are suitable for use in the invention have a non-zero vapour pressure (also known as the saturating vapour pressure), at room temperature, in particular a vapour pressure ranging from 0.3 Pa to 6000 Pa.

Preferably, the volatile linear alkane(s) that are suitable for use in the invention have a vapour pressure ranging from 0.3 to 2000 Pa, at room temperature (25° C.).

Preferably, the volatile linear alkane(s) that are suitable for use in the invention have a vapour pressure ranging from 0.3 to 1000 Pa, at room temperature (25° C.).

More preferably, the volatile linear alkane(s) that are suitable for use in the invention have a vapour pressure ranging from 0.4 to 600 Pa, at room temperature (25° C.).

Preferably, the volatile linear alkane(s) that are suitable for use in the invention have a vapour pressure ranging from 1 to 200 Pa, at room temperature (25° C.).

More preferably, the volatile linear alkane(s) that are suitable for use in the invention have a vapour pressure ranging from 3 to 60 Pa, at room temperature (25° C.).

According to one embodiment, the volatile linear alkane(s) that are suitable for use in the invention may have a flash point that is within the range from 30 to 120° C. and more particularly from 40 to 100° C. The flash point is in particular measured according to standard ISO 3679.

According to one embodiment, the volatile linear alkane(s) that are suitable for use in the invention may be linear alkanes comprising from 7 to 15 carbon atoms.

Preferably, the volatile linear alkane(s) that are suitable for use in the invention may be linear alkanes comprising from 8 to 14 carbon atoms.

Preferably, the volatile linear alkane(s) that are suitable for use in the invention may be linear alkanes comprising from 9 to 14 carbon atoms.

Preferably, the volatile linear alkane(s) that are suitable for use in the invention may be linear alkanes comprising from 10 to 14 carbon atoms.

Preferably, the volatile linear alkane(s) that are suitable for use in the invention may be linear alkanes comprising from 11 to 14 carbon atoms.

The volatile linear alkane(s) that are suitable for use in the invention may advantageously be of plant origin.

Preferably, the volatile linear alkane or the mixture of volatile linear alkanes present in the composition according to the invention comprises at least one $^{14}C$ (carbon-14) carbon isotope. In particular, the $^{14}C$ isotope may be present in a $^{14}C/^{12}C$ ratio of greater than or equal to $1\times10^{-16}$, preferably greater than or equal to $1\times10^{-15}$, more preferably greater than or equal to $7.5\times10^{-14}$ and better still greater than or equal to $1.5\times10^{-13}$. Preferably, the ratio $^{14}C/^{12}C$ ranges from $6\times10^{-13}$ to $1.2\times10^{-12}$ (numerical isotope ratio).

The amount of $^{14}C$ isotopes in the volatile linear alkane or the mixture of volatile linear alkanes may be determined via methods known to those skilled in the art such as the Libby counting method, liquid scintillation spectrometry or accelerator mass spectrometry.

Such an alkane may be obtained, directly or in several steps, from a plant raw material, such as an oil, a butter, a wax, etc.

As examples of volatile linear alkanes that are suitable for use in the invention, mention may be made of the alkanes described in patents WO 2007/068 371 or WO 2008/155 059 of the company Cognis (mixtures of different alkanes differing by at least one carbon). These alkanes are obtained from fatty alcohols, which are themselves obtained from coconut oil or palm oil.

As examples of volatile linear alkanes that are suitable for use in the invention, mention may be made of n-heptane ($C_7$), n-octane ($C_8$), n-nonane ($C_9$), n-decane ($C_{10}$), n-undecane ($C_{11}$), n-dodecane ($C_{12}$), n-tridecane ($C_{13}$) and n-tetradecane ($C_{14}$), and mixtures thereof. According to one particular embodiment, the volatile linear alkane is chosen from n-nonane, n-undecane, n-dodecane, n-tridecane and n-tetradecane, and mixtures thereof.

According to one preferred mode, mention may be made of mixtures of n-undecane ($C_{11}$) and of n-tridecane ($C_{13}$) obtained in Examples 1 and 2 of patent application WO 2008/155 059 of the company Cognis.

Mention may also be made of n-dodecane ($C_{12}$) and n-tetradecane ($C_{14}$) sold by Sasol under the references, respectively, Parafol 12-97 and Parafol 14-97, and also mixtures thereof.

The volatile linear alkane may also be used alone.

Alternatively or preferentially, a mixture of two different volatile linear alkanes, differing from each other by a carbon number n of at least 1, in particular differing from each other by a carbon number of 1 or 2, may be used.

According to one embodiment, a mixture of at least two different volatile linear alkanes comprising from 10 to 14 carbon atoms and differing from each other by a carbon number of at least 1 is used. Examples that may especially be mentioned include mixtures of $C_{10}/C_{11}$, $C_{11}/C_{12}$ or $C_{12}/C_{13}$ volatile linear alkanes.

According to another embodiment, a mixture of at least two different volatile linear alkanes comprising from 10 to 14 carbon atoms and differing from each other by a carbon number of at least 2 is used. Examples that may especially be mentioned include mixtures of $C_{10}/C_{12}$ or $C_{12}/C_{14}$ volatile linear alkanes, for an even carbon number n, and the $C_{11}/C_{13}$ mixture for an odd carbon number n.

According to one preferred mode, a mixture of at least two different volatile linear alkanes comprising from 10 to 14 carbon atoms and differing from each other by a carbon number of at least 2, and in particular a mixture of $C_{11}/C_{13}$ volatile linear alkanes or a mixture of $C_{12}/C_{14}$ volatile linear alkanes, is used.

Other mixtures combining more than two volatile linear alkanes according to the invention, for instance a mixture of at least three different volatile linear alkanes comprising from 7 to 15 carbon atoms and differing from each other by a carbon number of at least 1, also form part of the invention, but mixtures of two volatile linear alkanes according to the invention are preferred (binary mixtures), the two volatile linear alkanes preferably representing more than 95% and better still more than 99% by weight of the total content of volatile linear alkanes in the mixture.

According to one particular mode of the invention, in a mixture of volatile linear alkanes, the volatile linear alkane having the smaller carbon number is predominant in the mixture.

According to another mode of the invention, a mixture of volatile linear alkanes in which the volatile linear alkane having the larger carbon number is predominant in the mixture is used.

As examples of mixtures that are suitable for use in the invention, mention may be made especially of the following mixtures:

from 50% to 90% by weight, preferably from 55% to 80% by weight and more preferentially from 60% to 75% by weight of $C_n$ liquid volatile linear alkane with n ranging from 7 to 15, from 10% to 50% by weight, preferably from 20% to 45% by weight and preferably from 24% to 40% by weight of $C_{n+x}$ liquid volatile linear alkane with x greater than or equal to 1, preferably x=1 or x=2, with n+x between 8 and 14, relative to the total weight of alkanes in the mixture.

In particular, the mixture of volatile linear alkanes according to the invention may also contain:
- less than 2% by weight and preferably less than 1% by weight of branched hydrocarbons,
- and/or less than 2% by weight and preferably less than 1% by weight of aromatic hydrocarbons,
- and/or less than 2% by weight, preferably less than 1% by weight and preferentially less than 0.1% by weight of unsaturated hydrocarbons in the mixture.

More particularly, a volatile linear alkane that is suitable for use in the invention may be used in the form of an n-undecane/n-tridecane mixture.

In particular, a mixture of volatile linear alkanes will be used comprising:
- from 55% to 80% by weight and preferably from 60% to 75% by weight of $C_{11}$ volatile linear alkane (n-undecane),
- from 20% to 45% by weight and preferably from 24% to 40% by weight of $C_{13}$ volatile linear alkane (n-tridecane), relative to the total weight of alkanes in the mixture.

According to one particular embodiment, the mixture of alkanes is an n-undecane/n-tridecane mixture. In particular, such a mixture may be obtained according to Example 1 or Example 2 of WO 2008/155 059.

According to another particular embodiment, the n-dodecane sold under the reference Parafol 12-97 by Sasol is used.

According to another particular embodiment, the n-tetradecane sold under the reference Parafol 14-97 by Sasol is used.

According to yet another embodiment, a mixture of n-dodecane and n-tetradecane is used. It is in particular possible to use the dodecane/tetradecane mixture in an 85/15 weight ratio sold by the company Biosynthis under the reference Vegelight 1214.

The composition used according to the invention may comprise from 0.5% to 90% by weight, in particular from 1% to 50% by weight, more particularly from 1.5% to 40% by weight and better still from 2% to 30% by weight of one or more volatile linear alkanes relative to the total weight of the composition.

The volatile linear alkane(s) form, alone or with one or more other compounds listed below, the liquid fatty phase of the composition.

As explained previously, the composition used according to the invention comprises, besides the volatile linear alkane(s), one or more nonionic associative polymers.

For the purposes of the present invention, the term "polymer" means any compound derived from the polymerization by polycondensation or radical polymerization of monomers, at least one of which is other than an alkylene oxide, and of a monofunctional compound of formula RX, R denoting an optionally hydroxylated C10-C30 alkyl or alkenyl group, and X denoting a carboxylic acid, amine, amide, hydroxyl or ester group. Any compound derived exclusively from the simple condensation of an alkylene oxide with a fatty alcohol, a fatty ester, a fatty acid, a fatty amide or a fatty amine is in particular excluded.

It is recalled that associative polymers are amphiphilic polymers that are capable, in an aqueous medium, of reversibly combining with each other or with other molecules. Their chemical structure more particularly comprises at least one hydrophilic region and at least one hydrophobic region. The term "hydrophobic group" means a radical or polymer bearing a saturated or unsaturated, linear or branched hydrocarbon-based chain, comprising at least 8 carbon atoms, preferably from 10 to 30 carbon atoms, in particular from 12 to 30 carbon atoms and more preferentially from 18 to 30 carbon atoms. By way of example, the hydrophobic group may be derived from a fatty alcohol such as stearyl alcohol, dodecyl alcohol or decyl alcohol. It may also denote a hydrocarbon-based polymer, for instance polybutadiene.

The nonionic associative polymers are preferably chosen from:

(1) celluloses modified with groups comprising at least one fatty chain; examples that may be mentioned include:
- hydroxyethylcelluloses modified with groups comprising at least one fatty chain, such as alkyl, arylalkyl or alkylaryl groups, or mixtures thereof, and in which the alkyl groups are preferably $C_8$-$C_{22}$, for instance the product Natrosol Plus Grade 330 CS ($C_{16}$ alkyls) sold by the company Aqualon, or the product Bermocoll EHM 100 sold by the company Berol Nobel,
- those modified with alkylphenyl polyalkylene glycol ether groups, such as the product Amercell Polymer HM-1500 (nonylphenyl polyethylene glycol (15) ether) sold by the company Amerchol.

(2) hydroxypropyl guars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhodia.

(3) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208.

(4) copolymers of hydrophilic methacrylates or acrylates and of hydrophobic monomers comprising at least one fatty chain, such as, for example, the polyethylene glycol methacrylate/lauryl methacrylate copolymer.

(5) polyurethane polyethers comprising in their chain both hydrophilic blocks usually of polyoxyethylenated nature and hydrophobic blocks which may be aliphatic sequences alone and/or cycloaliphatic and/or aromatic sequences.

(6) polymers with an aminoplast ether backbone containing at least one fatty chain, such as the Pure Thix compounds sold by the company Sud-Chemie.

(7) copolymers of vinylpyrrolidone and of fatty-chain hydrophobic monomers; examples that may be mentioned include:
- the products Antaron V216 or Ganex V216 (vinylpyrrolidone/hexadecene copolymer) sold by the company ISP,
- the products Antaron V220 or Ganex V220 (vinylpyrrolidone/eicosene copolymer) sold by the company ISP.

Preferably, the polyurethane polyethers comprise at least two hydrocarbon-based lipophilic chains containing from 8 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or star polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205 containing a urea function, sold by the company Rheox, or Rheolate 208, 204 or 212, and also Acrysol RM 184, Aculyn 44 and Aculyn 46, from the company Röhm & Haas [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis (4-cyclohexylisocyanate) (SMDI), at 35% by weight in a mixture of propylene glycol (39%) and water (26%)].

Mention may also be made of the product Elfacos T210 containing a $C_{12-14}$ alkyl chain, and the product Elfacos T212 containing a $C_{18}$ alkyl chain, from Akzo.

The product DW 1206B from Röhm & Haas containing a $C_{20}$ alkyl chain and a urethane linkage, sold at a solids content of 20% in water, may also be used.

It is also possible to use solutions or dispersions of these polymers, especially in water or in aqueous-alcoholic medium. Examples of such polymers that may be mentioned are Rheolate 255, Rheolate 278 and Rheolate 244 sold by the company Rheox. The products DW 1206F and DW 1206J sold by the company Röhm & Haas may also be used.

Polyurethane-39 sold under the reference Luvigel Star by the company BASF may also be used.

The polyurethane polyethers that may be used according to the invention are in particular those described in the article by G. Fonnum, J. Bakke and F k. Hansen—Colloid Polym. Sci 271, 380.389 (1993).

The nonionic associative polymer(s) are preferably chosen from polyurethane polyethers.

The nonionic associative polymer(s) are preferably present in an amount ranging from 0.05% to 10% by weight, better still from 0.1% to 5% by weight and even more preferentially from 0.2% to 2% by weight relative to the total weight of the composition.

The composition used according to the invention may also comprise one or more non-silicone fatty substances.

Preferably, the non-silicone fatty substance(s) are chosen from fatty alcohols, fatty acids, fatty acid esters, fatty alcohol esters, waxes, and plant, animal, mineral and synthetic oils.

The fatty alcohols may be chosen from alcohols of formula R'OH, in which R' denotes a saturated or unsaturated, linear or branched radical, preferably comprising from 8 to 40 carbon atoms and preferably 8 to 30 carbon atoms. R' preferably denotes a $C_{12}$-$C_{24}$ alkyl or $C_{12}$-$C_{24}$ alkenyl group. R may be substituted with one or more hydroxyl groups.

The fatty alcohols may be chosen in particular from lauryl alcohol, cetyl alcohol, dodecyl alcohol, decyl alcohol, stearyl alcohol, oleyl alcohol, behenyl alcohol, linoleyl alcohol, undecylenyl alcohol, palmitoleyl alcohol, arachidonyl alcohol, myristyl alcohol and erucyl alcohol. A mixture of fatty alcohols may also be used, which means that several species of fatty alcohol may coexist, in the form of a mixture, in a commercial product. Mixtures of fatty alcohols that may be mentioned include cetylstearyl alcohol and cetearyl alcohol.

The fatty acids may be chosen from the acids of formula RCOOH, in which R is a saturated or unsaturated, linear or branched radical preferably comprising from 7 to 39 carbon atoms.

Preferably, R is a $C_7$-$C_{29}$ alkyl or $C_7$-$C_{29}$ alkenyl group and better still a $C_{12}$-$C_{24}$ alkyl or $C_{12}$-$C_{24}$ alkenyl group. R may be substituted with one or more hydroxyl groups and/or one or more carboxyl groups.

The fatty acid of the ester may be chosen in particular from lauric acid, oleic acid, palmitic acid, linoleic acid, myristic acid and stearic acid.

The waxes are natural (animal or plant) or synthetic substances that are solid at room temperature (20°-25° C.). They are insoluble in water, soluble in oils and are capable of forming a water-repellent film.

For the definition of waxes, mention may be made, for example, of P. D. Dorgan, Drug and Cosmetic Industry, December 1983, pp. 30-33.

The wax(es) that may be present in the composition used according to the invention may be chosen especially from carnauba wax, candelilla wax, esparto grass wax, paraffin wax, ozokerite, plant waxes such as olive tree wax, rice wax, hydrogenated jojoba wax or the absolute waxes of flowers such as the essential wax of blackcurrant blossom, animal waxes such as beeswaxes, or modified beeswaxes (cerabellina); other waxes or waxy starting materials that can be used according to the invention are, in particular, marine waxes such as the product sold by the company Sophim under the reference M82, and polyethylene waxes or polyolefins.

Plant oils that may be mentioned include jojoba oil, avocado oil, rapeseed oil, olive oil, sunflower oil, corn oil, soybean oil, marrow oil, grapeseed oil, sesame oil, hazelnut oil, apricot oil, macadamia oil, arara oil, sunflower oil and castor oil.

When they are present, the non-silicone fatty substance(s) generally represent from 0.5% to 20% by weight relative to the total weight of the composition.

The composition used according to the invention may also comprise one or more silicones.

The silicones that may be present in the composition according to the invention are in particular polyorganosiloxanes that may be in the form of aqueous solutions, i.e. dissolved, or optionally in the form of dispersions or microdispersions, or of aqueous emulsions. The polyorganosiloxanes may also be in the form of oils, waxes, resins or gums.

Organopolysiloxanes are defined in greater detail in Walter Noll's *Chemistry and Technology of Silicones* (1968), Academic Press.

The silicones may be volatile or non-volatile.

When they are volatile, the silicones are more particularly chosen from those with a boiling point of between 60° C. and 260° C., and even more particularly from:

(i) cyclic silicones containing from 3 to 7 and preferably 4 to 5 silicon atoms.

These are, for example, octamethylcyclotetrasiloxane sold in particular under the name Volatile Silicone 7207 by Union Carbide or Silbione 70045 V 2 by Rhône-Poulenc, decamethylcyclopentasiloxane sold under the name Volatile Silicone 7158 by Union Carbide, and Silbione 70045 V 5 by Rhône-Poulenc, and mixtures thereof.

Mention may also be made of cyclocopolymers of the dimethylsiloxanes/methylalkylsiloxane type, such as Volatile Silicone FZ 3109 sold by the company Union Carbide, with the chemical structure:

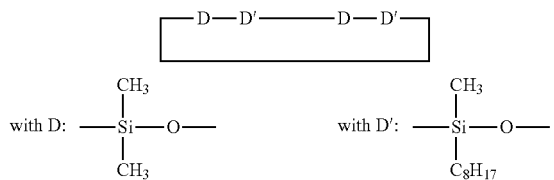

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^6$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers *Volatile Silicone Fluids for Cosmetics*.

Non-volatile silicones and more particularly polyalkylsiloxanes, polyarylsiloxanes, polyalkylarylsiloxanes, silicone gums and resins, and polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups (Dimethicone according to the CTFA name) having a viscosity of from $5 \times 10^{-6}$ to 2.5 m$^2$/s at 25° C. and preferably $1 \times 10^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:
  the Silbione oils of the 47 and 70 047 series or the Mirasil oils sold by Rhône-Poulenc, for instance the oil 70 047 V 500 000;
  the oils of the Mirasil series sold by the company Rhône-Poulenc;
  the oils of the 200 series from the company Dow Corning, such as, more particularly, DC200 with a viscosity of 60 000 cSt;
  the Viscasil oils from General Electric and certain oils of the SF series (SF 96, SF 18) from General Electric.

Mention may also be made of polydimethylsiloxanes containing dimethylsilanol end groups (Dimethiconol according to the CTFA name) such as the oils of the 48 series from the company Rhône-Poulenc.

Mention may also be made of polydimethylsiloxanes containing aminoethyl aminopropyl and α,ω-silanol.

In this category of polyalkylsiloxanes, mention may also be made of the products sold under the names Abil Wax 9800 and 9801 by the company Goldschmidt, which are poly($C_1$-$C_{20}$)alkylsiloxanes.

The polyalkylarylsiloxanes are particularly chosen from linear and/or branched polydimethyl methylphenyl siloxanes and polydimethyl diphenylsiloxanes with a viscosity of from $1 \times 10^{-5}$ to $5 \times 10^{-2}$ m$^2$/s at 25° C.

Among these polyalkylarylsiloxanes, examples that may be mentioned include the products sold under the following names:
  the Silbione oils of the 70 641 series from Rhône-Poulenc;
  the oils of the Rhodorsil 70 633 and 763 series from Rhône-Poulenc;
  the oil Dow Corning 556 Cosmetic Grade Fluid from Dow Corning;
  the silicones of the PK series from Bayer, such as the product PK20;
  the silicones of the series PN and PH from Bayer, such as the products PN1000 and PH1000;
  certain oils of the SF series from General Electric, such as SF 1023, SF 1154, SF 1250 and SF 1265.

The silicone gums that may be present in the composition used according to the invention are especially polydiorganosiloxanes having high number-average molecular masses of between 200 000 and 1 000 000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane and tridecanes, or mixtures thereof.

Mention may be made more particularly of the following products:
  polydimethylsiloxane gums,
  polydimethylsiloxane/methylvinylsiloxane gums,
  polydimethylsiloxane/diphenylsiloxane gums,
  polydimethylsiloxane/phenylmethylsiloxane gums,
  polydimethylsiloxane/diphenylsiloxane/methylvinylsiloxane gums.

Products that may be used more particularly are the following mixtures:
  mixtures formed from a polydimethylsiloxane hydroxylated at the end of the chain (known as dimethiconol according to the nomenclature of the CTFA dictionary) and of a cyclic polydimethylsiloxane (known as cyclomethicone according to the nomenclature of the CTFA dictionary), such as the product Q2 1401 sold by the company Dow Corning;
  mixtures formed from a polydimethylsiloxane gum with a cyclic silicone, such as the product SF 1214 Silicone Fluid from the company General Electric, this product being an SF 30 gum corresponding to a dimethicone, having a number-average molecular weight of 500 000, dissolved in the oil SF 1202 Silicone Fluid corresponding to decamethylcyclopentasiloxane;
  mixtures of two PDMSs of different viscosities, and more particularly of a PDMS gum and a PDMS oil, such as the product SF 1236 from the company General Electric. The product SF 1236 is a mixture of an SE 30 gum defined above, with a viscosity of 20 m$^2$/s, and of an SF 96 oil with a viscosity of $5 \times 10^{-6}$ m$^2$/s. This product preferably comprises 15% SE 30 gum and 85% of an SF 96 oil.

The organopolysiloxane resins that may be present in the composition used according to the invention are crosslinked siloxane systems containing the following units: $R_2SiO_{2/2}$, $R_3SiO_{1/2}$, $RSiO_{3/2}$ and $SiO_{4/2}$ in which R represents a hydrocarbon group containing 1 to 16 carbon atoms or a phenyl group. Among these products, those particularly preferred are the ones in which R denotes a $C_1$-$C_4$ lower alkyl radical, more particularly methyl, or a phenyl radical.

Among these resins, mention may be made of the product sold under the name Dow Corning 593 or those sold under the names Silicone Fluid SS 4230 and SS 4267 by the company General Electric, which are silicones of dimethyl/trimethyl siloxane structure.

Mention may also be made of the trimethyl siloxysilicate type resins sold in particular under the names X22-4914, X21-5034 and X21-5037 by the company Shin-Etsu.

The organomodified silicones that may be present in the composition according to the invention are silicones as defined above and containing in their structure one or more organofunctional groups attached via a hydrocarbon-based radical.

Among the organomodified silicones, mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils Silwet L 722, L 7500, L 77 and L 711 by the company Union Carbide, and the ($C_{12}$)alkylmethicone copolyol sold by the company Dow Corning under the name Q2 5200;

thiol groups, such as the products sold under the names GP 72 A and GP 71 from Genesee;

alkoxylated groups, such as the product sold under the name Silicone Copolymer F-755 by SWS Silicones and Abil Wax 2428, 2434 and 2440 by the company Goldschmidt;

hydroxylated groups, such as the polyorganosiloxanes containing a hydroxyalkyl function, described in French patent application FR-A-85/16334;

acyloxyalkyl groups, such as, for example, the polyorganosiloxanes described in U.S. Pat. No. 4,957,732;

anionic groups of the carboxylic acid type, such as, for example, in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names Abil S201 and Abil S255;

hydroxyacylamino groups, such as the polyorganosiloxanes described in patent application EP 342 834. Mention may be made, for example, of the product Q2-8413 from the company Dow Corning.

Among the organomodified silicones, mention may also be made of amino silicones.

The term "amino silicone" means any silicone comprising at least one primary, secondary or tertiary amine function or one or more quaternary ammonium groups.

The amino silicones that may be used in the cosmetic composition according to the present invention are chosen from:

(a) the compounds corresponding to formula (I) below:

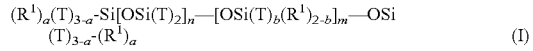

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, n possibly denoting a number from 0 to 1999 and especially from 49 to 149, and m possibly denoting a number from 1 to 2000 and especially from 1 to 10;

$R^1$ is a monovalent radical of formula —$C_qH_{2q}$L in which q is a number from 2 to 8 and L is an optionally quaternized amino group chosen from the following groups:

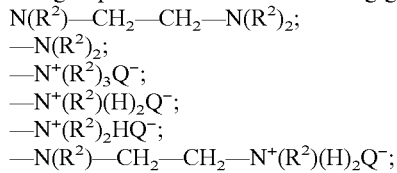

in which $R^2$ can denote a hydrogen atom, a phenyl, a benzyl or a saturated monovalent hydrocarbon-based radical, for example a $C_1$-$C_{20}$ alkyl radical, and $Q^-$ represents a halide ion such as, for example, fluoride, chloride, bromide or iodide.

In particular, the amino silicones corresponding to the definition of formula (I) are chosen from the compounds corresponding to the following formula:

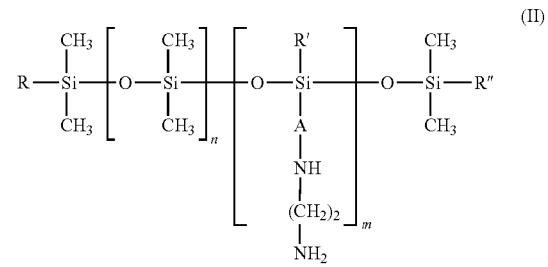

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxyl/alkoxy molar ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxyl/alkoxy molar ratio is preferably between 1/0.8 and 1/1.1 and is advantageously equal to 1/0.95. Moreover, m and n are such that the weight-average molecular mass of the compound is between 2000 and 200

000. More particularly, n is between 0 and 999 and m is between 1 and 1000, the sum of n and m being between 1 and 1000.

More particularly, mention may be made of the product Fluid WR® 1300 sold by the company Wacker.

It should be noted that the molecular mass of these silicones is determined by gel permeation chromatography (ambient temperature, polystyrene standard; μ styragem columns; eluent THF; flow rate 1 mm/m; 200 μl of a solution containing 0.5% by weight of silicone are injected into THF and detection is performed by refractometry and UV-metry).

A product corresponding to the definition of formula (I) is in particular the polymer known in the CTFA dictionary as "trimethylsilyl amodimethicone", corresponding to formula (III) below:

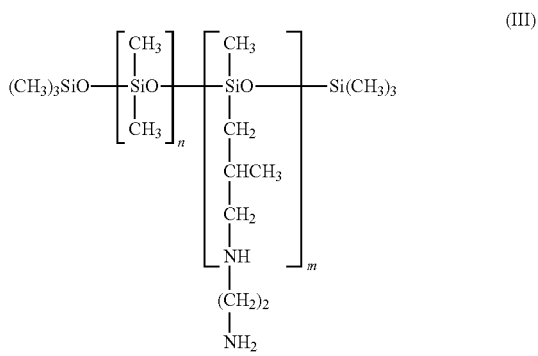

in which n and m have the meanings given above in accordance with formula (I).

Such compounds are described, for example, in patent application EP95238; a compound of formula (III) is sold, for example, under the name Q2-8220 by the company OSI.

(b) the compounds corresponding to formula (IV) below:

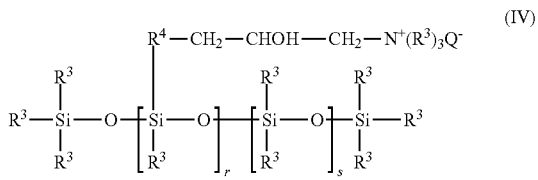

in which:

$R^3$ represents a monovalent $C_1$-$C_{18}$ hydrocarbon-based radical, and in particular a $C_1$-$C_{18}$ alkyl or $C_2$-$C_{18}$ alkenyl radical, for example methyl;

$R^4$ represents a divalent hydrocarbon-based radical, especially a $C_1$-$C_{18}$ alkylene radical or a divalent $C_1$-$C_{18}$, and for example $C_1$-$C_8$, alkyleneoxy radical;

$Q^-$ is a halide ion, especially chloride;

r represents an average statistical value from 2 to 20 and in particular from 2 to 8;

s represents an average statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) the quaternary ammonium silicones of formula (V):

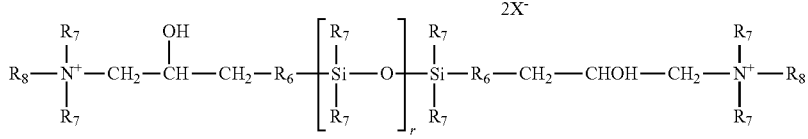

in which:

$R_7$, which may be identical or different, represents a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, especially a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represents a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—$NHCOR_7$;

$X^-$ is an anion such as a halide ion, especially chloride, or an organic acid salt (acetate, etc.);

r represents a mean statistical value from 2 to 200 and in particular from 5 to 100.

These silicones are described, for example, in patent application EP-A 0 530 974.

(d) the amino silicones of formula (VI):

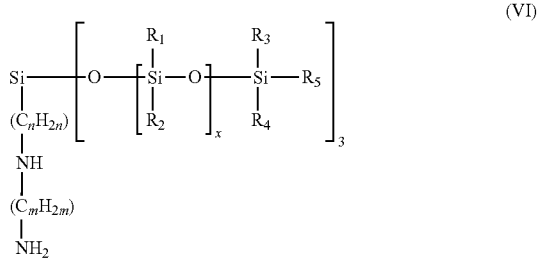

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and in which x is chosen such that the amine number is between 0.01 and 1 meq./g.

The silicones that are particularly preferred are polydimethylsiloxanes, dimethicones and amodimethicones.

When these compounds are used, one particularly advantageous embodiment involves their joint use with cationic and/or nonionic surfactants.

By way of example, use may be made of the product sold under the name Cationic Emulsion DC 939 by the company Dow Corning, which comprises, besides amodimethicone, a cationic surfactant which is trimethylcetylammonium chloride and a nonionic surfactant of formula: $C_{13}H_{27}$—$(OC_2H_4)_{12}$—OH, known under the CTFA name Trideceth-12.

Another commercial product that may be used according to the invention is the product sold under the name Dow Corning Q2 7224 by the company Dow Corning, comprising, in combination, the trimethylsilyl amodimethicone of formula (III) described above, a nonionic surfactant of formula: $C_8H_{17}$—$C_6H_4$—$(OCH_2CH_2)_{40}$—OH, known under the CTFA name octoxynol-40, a second nonionic surfactant of formula: $C_{12}H_{25}$—$(OCH_2$—$CH_2)_6$—OH, known under the CTFA name Isolaureth-6, and propylene glycol.

The silicone(s) generally represent 0.1% to 20% and preferably from 0.1% to 10% by weight relative to the total weight of the composition.

The cosmetic composition used according to the invention may also comprise one or more polymers other than the nonionic associative polymers described above.

The polymer(s) other than the nonionic associative polymers described above may be of natural, plant, mineral and/or synthetic origin.

The polymers of natural origin may be chosen from pectins, celluloses, alginates, galactoarabinan, gum tragacanth, starches and sucrose.

The synthetically modified polymers of plant origin may be chosen, for example, from starch derivatives, such as carboxymethylstarch and distarch phosphate, and cellulose derivatives such as hydroxyethylcellulose and carboxymethylcellulose.

The polymers may be chosen from cationic, anionic, amphoteric and nonionic polymers.

The cationic polymers are most particularly advantageous as agents for conditioning keratin fibres.

For the purposes of the present invention, the term "cationic polymer" means any polymer comprising cationic groups and/or groups that may be ionized into cationic groups.

The cationic polymers that may be used according to the present invention are preferably chosen from polymers comprising primary, secondary, tertiary and/or quaternary amine groups forming part of the polymer chain or directly attached thereto, and having a number average molecular weight of between 500 and about 5 000 000 and preferably between 1000 and 3 000 000.

Among these polymers, mention may be made more particularly of the following cationic polymers:

(1) Homopolymers or copolymers derived from acrylic or methacrylic esters or amides with amine functions, and comprising at least one of the units of the following formulae:

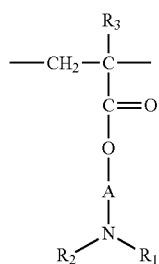

(A)

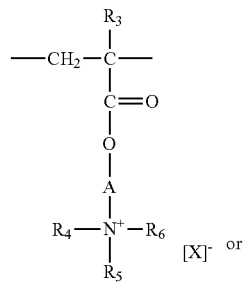

(B)

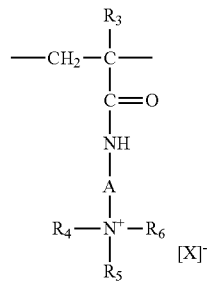

(C)

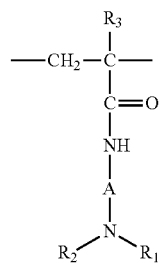

(D)

in which:

$R_1$ and $R_2$, which may be identical or different, each represent a hydrogen atom or an alkyl group having from 1 to 6 carbon atoms;

$R_3$ denotes a hydrogen atom or a group $CH_3$;

A is a linear or branched alkyl group comprising 1 to 6 carbon atoms or a hydroxyalkyl group comprising 1 to 4 carbon atoms;

$R_4$, $R_5$ and $R_6$, which may be identical or different, represent an alkyl group having from 1 to 18 carbon atoms or a benzyl group;

X denotes a methosulfate anion or a halide such as chloride or bromide.

The copolymers of the family (1) also contain one or more comonomer units that may be chosen from the family of acrylamides, methacrylamides, diacetone acrylamides, acrylamides and methacrylamides substituted on the nitrogen with lower ($C_{1-4}$) alkyl groups, groups derived from acrylic or methacrylic acids or esters thereof, vinyllactams such as vinylpyrrolidone or vinylcaprolactam, and vinyl esters.

Thus, among these copolymers of the family (1), mention may be made of:

copolymers of acrylamide and of dimethylaminoethyl methacrylate quaternized with dimethyl sulfate or with a dimethyl halide, such as the one sold under the name Hercofloc® by the company Hercules, copolymers of acrylamide and of methacryloyloxyethyl-trimethylammonium chloride, described, for example, in patent application EP-A-080 976 and sold under the name Bina Quat P 100 by the company Ciba Geigy, copolymers of acrylamide and of methacryloyloxyethyl-trimethylammonium methosulfate, such as the product sold under the name Reten by the company Hercules, quaternized or non-quaternized vinylpyrrolidone/dialkylaminoalkyl acrylate or methacrylate copolymers, such as the products sold under the name Gafquat® by the company ISP, such as, for example, Gafquat® 734 or Gafquat® 755, or alternatively the products known as Copolymer® 845, 958 and 937. These polymers are described in detail in French patents 2 077 143 and 2 393 573, dimethylaminoethyl methacrylate/vinylcaprolactam/vinylpyrrolidone terpolymers, such as the product sold under the name Gaffix® VC 713 by the company ISP, quaternized vinylpyrrolidone/dimethylaminopropylmethacrylamide copolymers, such as the product sold under the name Gafquat® HS 100 by the company ISP; and crosslinked polymers of methacryloyloxy($C_1$-$C_4$)alkyltri($C_1$-$C_4$)alkyl-ammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the copolymer in mineral oil can be used more particularly. This dispersion is sold under the name Salcare® SC 92 by the company Ciba. A crosslinked methacryloyloxyethyltrimethylammonium chloride homopolymer containing about 50% by weight of the homopolymer in mineral oil or in a liquid ester can also be used. These dispersions are sold under the names Salcare® SC 95 and Salcare® SC 96 by the company Ciba.

(2) Cationic polysaccharides, and in particular those chosen from:

a) cellulose ether derivatives containing quaternary ammonium groups, described in French patent 1 492 597 and in particular the polymers sold under the names Ucare Polymer "JR" (JR 400 LT, JR 125 or JR 30M) or "LR" (LR 400 or LR 30M) by the company Amerchol. These polymers are also defined in the CTFA dictionary as quaternary ammoniums of hydroxyethylcellulose that have reacted with an epoxide substituted with a trimethylammonium group;

b) cellulose derivatives grafted with a water-soluble monomer of quaternary ammonium, and described especially in U.S. Pat. No. 4,131,576, such as hydroxyalkylcelluloses, for instance hydroxymethyl-, hydroxyethyl- or hydroxypropyl-celluloses grafted, in particular, with a methacryloylethyl-trimethylammonium, methacrylamidopropyl-trimethylammonium or dimethyldiallylammonium salt.

The commercial products corresponding to this definition are more particularly the products sold under the names Celquat L 200 and Celquat H 100 by the company National Starch.

c) cationic polygalactomannans such as those described in U.S. Pat. Nos. 3,589,578 and 4,031,307, such as guar gums containing cationic trialkylammonium groups. Such products are sold in particular under the trade names Jaguar C13 S, Jaguar C 15 and Jaguar C 17 by the company Rhodia.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers. Such polymers are described, in particular, in French patents 2 162 025 and 2 280 361.

(4) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(5) Polyamino amide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl group comprises from 1 to 4 carbon atoms and preferably denotes a methyl, ethyl or propyl group, and the alkylene group comprises from 1 to 4 carbon atoms, and preferably denotes an ethylene group. Such polymers are described in particular in French patent 1 583 363.

Among these derivatives, mention may be made more particularly of the adipic acid/dimethylaminohydroxypropyl/diethylenetriamine polymers.

(6) Polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The mole ratio between the polyalkylene polyamine and the dicarboxylic acid is between 0.8:1 and 1.4:1; the polyamino amide resulting therefrom is reacted with epichlorohydrin in a mole ratio of epichlorohydrin relative to the secondary amine group of the polyamino amide of between 0.5:1 and 1.8:1. Such polymers are described in particular in U.S. Pat. Nos. 3,227,615 and 2,961,347.

(7) Cyclopolymers of alkyldiallylamine or of dialkyldiallylammonium, such as homopolymers or copolymers comprising, as main constituent of the chain, units corresponding to formula (VIIa) or (VIIb):

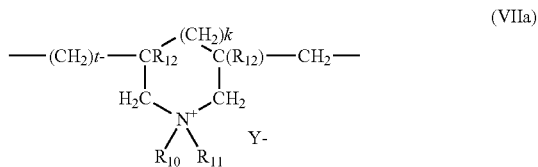
(VIIa)

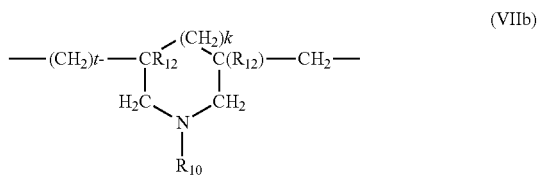
(VIIb)

in which k and t are equal to 0 or 1, the sum k+t being equal to 1; $R_{12}$ denotes a hydrogen atom or a methyl radical; $R_{10}$ and $R_{11}$, independently of each other, denote an alkyl group containing from 1 to 6 carbon atoms, a hydroxyalkyl group in which the alkyl group preferably contains 1 to 5 carbon atoms, or a lower ($C_1$-$C_4$) amidoalkyl group, or $R_{10}$ and $R_{11}$ may denote, together with the nitrogen atom to which they are attached, heterocyclic groups, such as piperidyl or morpholinyl; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

$R_{10}$ and $R_{11}$, independently of each other, preferably denote an alkyl group containing from 1 to 4 carbon atoms.

Among the polymers defined above, mention may be made more particularly of the dimethyldiallylammonium chloride homopolymer sold under the name Merquat® 100 by the company Nalco (and its homologues of low weight-average molecular mass) and the copolymers of diallyldimethylammonium chloride and of acrylamide, sold under the names Merquat® 550 and Merquat® 7SPR.

(8) The quaternary diammonium polymer containing repeating units corresponding to formula (VIII):

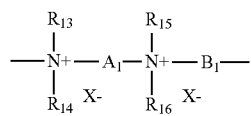

(VIII)

in which:

$R_{13}$, $R_{14}$, $R_{15}$ and $R_{16}$, which may be identical or different, represent aliphatic, alicyclic or arylaliphatic groups containing from 1 to 20 carbon atoms or lower hydroxyalkylaliphatic groups, or alternatively $R_{13}$, $R_{14}$, $R_{15}$ and $R_{16}$, together or separately, constitute, with the nitrogen atoms to which they are attached, heterocycles optionally containing a second heteroatom other than nitrogen, or alternatively $R_{13}$, $R_{14}$, $R_{15}$ and $R_{16}$ represent a linear or branched $C_1$-$C_6$ alkyl group substituted with a nitrile, ester, acyl or amide group or a group —CO—O—$R_{17}$-E or —CO—NH—$R_{17}$-E where $R_{17}$ is an alkylene and E is a quaternary ammonium group;

$A_1$ and $B_1$ represent polymethylene groups containing from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{13}$ and $R_{15}$ can form, with the two nitrogen atoms to which they are attached, a piperazine ring; in addition, if $A_1$ denotes a linear or branched, saturated or unsaturated alkylene or hydroxyalkylene group, $B_1$ can also denote a group:

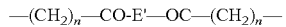

in which E' denotes:

a) a glycol residue of formula: —O—Z—O—, where Z denotes a linear or branched hydrocarbon-based group or a group corresponding to one of the following formulae:

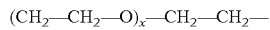

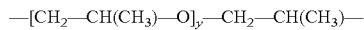

where x and y denote an integer from 1 to 4, representing a defined and unique degree of polymerization or any number from 1 to 4 representing an average degree of polymerization; or b) a bis-secondary diamine residue such as a piperazine derivative; or c) a bis-primary diamine residue of formula —NH—Y—NH—, where Y denotes a linear or branched hydrocarbon-based radical, or alternatively the divalent group —$CH_2$—$CH_2$—S—S—$CH_2$—$CH_2$—; or d) a ureylene group of formula: —NH—CO—NH—.

Preferably, $X^-$ is an anion such as chloride or bromide.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that are formed from repeating units corresponding to formula (IX):

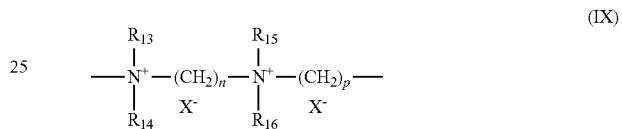

(IX)

in which $R_{13}$, $R_{14}$, $R_{15}$ and $R_{16}$, which may be identical or different, denote an alkyl or hydroxyalkyl group containing from 1 to 4 carbon atoms approximately, n and p are integers ranging from 2 to 20 approximately, and $X^-$ is an anion derived from a mineral or organic acid.

(9) Polyquaternary ammonium polymers formed from repeating units of formula (X):

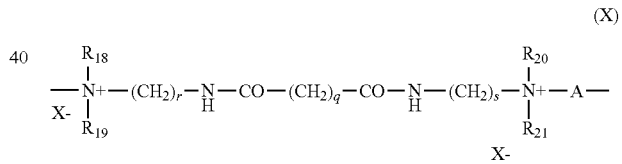

(X)

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$(OCH$_2$CH$_2$)$_p$OH group, where p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, $X^-$ denotes an anion such as a halide, A denotes a dihalide radical or preferably represents —$CH_2$—$CH_2$—O—$CH_2$—$CH_2$—.

Such compounds are especially described in patent application EP-A-122 324.

(10) Quaternary polymers of vinylpyrrolidone and of vinylimidazole, for instance the products sold under the names Luviquat FC 905, FC 550 and FC 370 by the company BASF.

(11) Chitosans or salts thereof; the salts that can be used are, in particular, chitosan acetate, lactate, glutamate, gluconate or pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

Other cationic polymers that may be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Polymer blends may also be used.

The cationic polymers of families (1) and (7) are particularly preferred.

The composition used according to the invention may also comprise, as polymers, one or more modified or unmodified starches.

The starch(es) that may be present in the composition used according to the invention are more particularly macromolecules in the form of polymers formed from elemental units that are anhydroglucose units. The number of these units and their assembly makes it possible to distinguish amylose (linear polymer) and amylopectin (branched polymer). The relative proportions of amylose and of amylopectin, and also their degree of polymerization, vary as a function of the botanical origin of the starches.

The starch molecules that may be used in the present invention may originate from a botanical source such as cereals, tubers, roots, legumes and fruit. Thus, the starch(es) may originate from a botanical source chosen from corn, pea, potato, sweet potato, banana, barley, wheat, rice, oat, sago, tapioca and sorghum. The starch is preferably derived from potato.

Hydrolysates of the starches mentioned above may also be used.

The starches are generally in the form of a white powder, which is insoluble in cold water, whose elemental particle size ranges from 3 to 100 microns.

The starches that may be used in the composition used according to the invention may be chemically modified via one or more of the following reactions: pregelatinization, oxidation, crosslinking, esterification, heat treatments.

More particularly, these reactions may be performed in the following manner:
- pregelatinization by splitting the starch granules (for example drying and cooking in a drying drum);
- oxidation with strong oxidizing agents leading to the introduction of carboxyl groups into the starch molecule and to depolymerization of the starch molecule (for example by treating an aqueous starch solution with sodium hypochlorite);
- crosslinking with functional agents capable of reacting with the hydroxyl groups of the starch molecules, which will thus bind together (for example with glyceryl and/or phosphate groups);
- esterification in alkaline medium for the grafting of functional groups, especially C1-C6 acyl (acetyl), C1-C6 hydroxyalkyl (hydroxyethyl, hydroxypropyl), carboxyalkyl (in particular carboxymethyl) or octenylsuccinic. Mention may be made in particular of starches modified with sodium carboxymethyl.

Monostarch phosphates (of the type Am—O—PO—(OX)2), distarch phosphates (of the type Am—O—PO—(OX)—O—Am) or even tristarch phosphates (of the type Am—O—PO—(O—Am)2) or mixtures thereof, may especially be obtained by crosslinking with phosphorus compounds.

X especially denotes alkali metals (for example sodium or potassium), alkaline-earth metals (for example calcium or magnesium), ammonium salts, amine salts such as those of monoethanolamine, diethanolamine, triethanolamine or 3-amino-1,2-propanediol, and ammonium salts derived from basic amino acids such as lysine, arginine, sarcosine, ornithine or citrulline.

The phosphorus compounds may be, for example, sodium tripolyphosphate, sodium orthophosphate, phosphorous oxychloride or sodium trimetaphosphate.

Use will preferentially be made of distarch phosphates, in particular hydroxypropyl distarch phosphates, or of compounds rich in distarch phosphate, especially hydroxypropyl distarch phosphate, for instance the product sold under the references Prejel VA-70-T AGGL (gelatinized hydroxypropyl cassava distarch phosphate) or Prejel TK1 (gelatinized cassava distarch phosphate) or Prejel 200 (gelatinized acetyl cassava distarch phosphate) by the company Avebe, or Structure Zea from National Starch (gelatinized hydroxypropyl corn distarch phosphate).

When the starches are chemically modified via an esterification reaction, carboxyalkylstarches may be obtained, as indicated previously.

The carboxyalkylstarches are preferably carboxy($C_1$-$C_4$) alkylstarches and more particularly carboxymethylstarches.

The salts are especially salts of an alkali metal or an alkaline-earth metal such as Na, K 1/2, Li, $NH_4$, of a quaternary ammonium or of an organic amine such as monoethanolamine, diethanolamine or triethanolamine.

Carboxyalkylstarches are obtained by grafting carboxyalkyl groups onto one or more alcohol functions of the starch, especially by reaction of starch and of sodium monochloroacetate in alkaline medium.

The carboxyalkyl groups are generally attached via an ether function, more particularly to carbon 1.

The degree of substitution preferably ranges from 0.1 to 1 and more particularly from 0.15 to 0.5. The degree of substitution is defined according to the present invention as being the average number of hydroxyl groups substituted with an ester or ether group (in the present case ether for the carboxymethylstarches) per monosaccharide unit of the polysaccharide.

The carboxyalkylstarches preferably comprise units having the following formula:

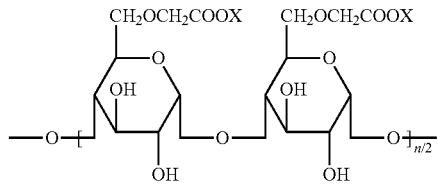

X denotes a hydrogen atom, an alkali metal or alkaline-earth metal such as Na, K 1/2, Li, $NH_4$, a quaternary ammonium or an organic amine. Preferably, X denotes an $Na^+$ ion.

The carboxyalkylstarches that may be used according to the present invention are preferably non-pregelatinized carboxyalkylstarches.

The carboxyalkylstarches that may be used according to the present invention are preferably partially or totally crosslinked carboxyalkylstarches.

The carboxyalkylstarches that may be used according to the present invention are preferably sodium salts of carboxyalkylstarches, in particular a sodium salt of potato carboxymethylstarch, sold especially under the name Primojel by the company DMV International. More than 95% of the particles of this starch have a diameter of less than 100 microns and more particularly less than 65 microns.

According to the invention, it is also possible to use amphoteric starches, these amphoteric starches containing one or more anionic groups and one or more cationic groups. The anionic and cationic groups may be attached to the same reactive site of the starch molecule or to different reactive sites; they are preferably attached to the same reactive site. The anionic groups may be of carboxylic, phosphate or sulfate type, preferably of carboxylic type. The cationic groups may be of primary, secondary, tertiary or quaternary amine type.

The amphoteric starches are especially chosen from the compounds having the following formulae:

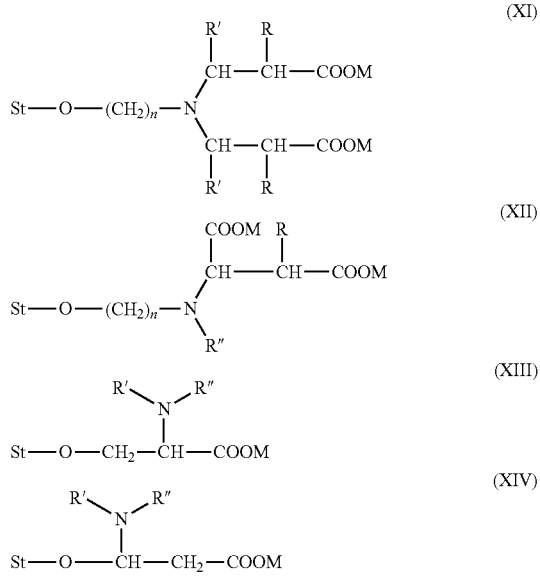

in which formulae:
St-O represents a starch molecule,
R, which may be identical or different, represents a hydrogen atom or a methyl radical,
R', which may be identical or different, represents a hydrogen atom, a methyl radical or a group —COOH,
n is an integer equal to 2 or 3,
M, which may be identical or different, denotes a hydrogen atom, an alkali metal or alkaline-earth metal such as Na, K or Li, $NH_4$, a quaternary ammonium or an organic amine,
R″ represents a hydrogen atom or an alkyl radical containing from 1 to 18 carbon atoms.

These compounds are especially described in U.S. Pat. No. 5,455,340 and U.S. Pat. No. 4,017,460, which are included herein by reference.

The starches of formula (XI) or (XII) are particularly used. Starches modified with 2-chloroethylaminodipropionic acid, i.e. the starches of formula (XI) or (XII) in which R, R', R″ and M represent a hydrogen atom and n is equal to 2, are more particularly used. Mention may be made in particular of the potato starch modified with 2-chloroethylaminodipropionic acid neutralized with sodium hydroxide, sold under the reference Structure Solanace by the company National Starch.

Preferably, the starch(es) that may be used in the invention are chemically modified.

The polymer(s) other than the nonionic associative polymers described previously generally represent from 0 to 20% and preferably from 0.2% to 10% by weight relative to the total weight of the composition.

The composition used according to the invention may also comprise one or more anionic, cationic, amphoteric and/or nonionic surfactants.

Among the anionic surfactants that may be used in the compositions according to the invention, mention may be made especially of salts, in particular alkali metal salts, and especially sodium salts, ammonium salts, amine salts, amino alcohol salts or magnesium salts of the following compounds: alkyl sulfates, alkyl ether sulfates, alkylamido ether sulfates, monoglyceride sulfates, alkylglyceryl sulfonates, alkyl sulfonates, alkyl phosphates, alkylamide sulfonates, alkylarylsulfonates, α-olefin sulfonates, paraffin sulfonates, alkylsulfosuccinates, alkyl ether sulfosuccinates, alkylamide sulfosuccinates, alkyl sulfosuccinamates, alkyl sulfoacetates, alkyl ether phosphates, acyl isethionates, N-acyltaurates, N-acylamino acids such as N-acylsarcosinates and N-acylglutamates. As anionic surfactants that may be used in the compositions according to the invention, mention may also be made of fatty acid salts such as salts of undecenylic acid, oleic acid, ricinoleic acid, palmitic acid and stearic acid, coconut oil acid or hydrogenated coconut oil acid and acylhydroxy acids such as acyl lactylates. It is also possible to use weakly anionic surfactants such as alkyl D-galactoside uronic acids and salts thereof, and also polyoxyalkylenated alkyl ether alkylamido ether carboxylic acids or salts thereof, the alkyl or acyl radical of these various compounds preferably comprising from 8 to 22 carbon atoms, and anionic derivatives of ($C_8$-$C_{22}$) alkyl polyglycosides (sulfate, sulfosuccinate, phosphate, isethionate, ether carboxylate, carbonate).

Among the amphoteric surfactants that may especially be mentioned are secondary or tertiary aliphatic amine derivatives, in which the aliphatic radical is a linear or branched chain comprising 8 to 22 carbon atoms and containing at least one hydrosolubilizing anionic group, for instance a carboxylate, sulfonate, sulfate, phosphate or phosphonate group. Among the surfactants of amphoteric or zwitterionic type, mention may also be made of sulfobetaines, alkylamidoalkylbetaines, alkylamidoalkylsulfobetaines and imidazolium derivatives such as those of amphocarboxyglycinate or of amphocarboxypropionate.

Among the nonionic surfactants that may be used according to the invention, mention may be made especially of polyethoxylated, polypropoxylated or polyglycerolated derivatives of alcohols, of α-diols or of alkylphenols or of fatty acids, with a fatty chain comprising from 8 to 28 carbon atoms, the number of ethylene oxide or propylene oxide groups possibly ranging from 2 to 50 and the number of glycerol groups especially ranging from 2 to 30. Mention may also be made of copolymers of ethylene oxide and of propylene oxide, condensates of ethylene oxide and of propylene oxide with fatty alcohols, polyethoxylated fatty amides preferably containing from 2 to 30 mol of ethylene oxide, polyglycerolated fatty amides containing on average 1 to 5 glycerol groups, polyglycerolated diglycolamides, optionally oxyethylenated fatty acid esters of sorbitan, fatty acid esters of sucrose, polyoxyalkylenated fatty acid esters, optionally oxyalkylenated alkylpolyglycosides, alkylglucoside esters, N-alkylglucamine and N-acylmethylglucamine derivatives, aldobionamides and amine oxides.

Cationic surfactants that may be mentioned in particular (non-limiting list) include: primary, secondary or tertiary fatty amine salts, optionally polyoxyalkylenated; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives.

Cationic surfactants that may also be used are quaternary ammonium salts containing at least one ester function, such as those of formula (XV) below:

$$R_{24}-\overset{O}{\underset{}{\overset{\|}{C}}}-(OC_rH_{2r})_y-\underset{R_{22}}{\overset{(C_sH_{2s}O)_z-R_{25}}{\overset{|}{N^+}}}-(C_tH_{2t}O)_x-R_{23} \quad X^-$$

(XV)

in which:

$R_{22}$ is chosen from $C_1$-$C_6$ alkyl radicals and $C_1$-$C_6$ hydroxyalkyl or dihydroxyalkyl radicals;

$R_{23}$ is chosen from:
the radical $$R_{26}-\overset{O}{\underset{}{\overset{\|}{C}}}-$$

linear or branched, saturated or unsaturated $C_1$-$C_{22}$ hydrocarbon-based radicals $R_{27}$,
a hydrogen atom, $R_{25}$ is chosen from:
the radical $$R_{28}-\overset{O}{\underset{}{\overset{\|}{C}}}-$$

linear or branched, saturated or unsaturated $C_1$-$C_6$ hydrocarbon-based radicals $R_{29}$,
a hydrogen atom, $R_{24}$, $R_{26}$ and $R_{28}$, which may be identical or different, are chosen from linear or branched, saturated or unsaturated $C_7$-$C_{21}$ hydrocarbon-based radicals;

r, s and t, which may be identical or different, are integers ranging from 2 to 6;

y is an integer ranging from 1 to 10;

x and z, which may be identical or different, are integers ranging from 0 to 10;

$X^-$ is a simple or complex, organic or inorganic anion;

with the proviso that the sum x+y+z ranges from 1 to 15, that when x is 0, then $R_{23}$ denotes $R_{27}$ and that when z is 0, then $R_{25}$ denotes $R_{29}$.

The alkyl radicals $R_{22}$ may be linear or branched and more particularly linear.

Preferably, $R_{22}$ denotes a methyl, ethyl, hydroxyethyl or dihydroxypropyl radical and more particularly a methyl or ethyl radical.

Advantageously, the sum x+y+z ranges from 1 to 10.

When $R_{23}$ is a hydrocarbon-based radical $R_{27}$, it may be long and contain from 12 to 22 carbon atoms, or short and contain from 1 to 3 carbon atoms.

When $R_{25}$ is a hydrocarbon-based radical $R_{29}$, it preferably contains 1 to 3 carbon atoms.

Advantageously, $R_{24}$, $R_{26}$ and $R_{28}$, which may be identical or different, are chosen from linear or branched, saturated or unsaturated $C_{11}$-$C_{21}$ hydrocarbon-based radicals and more particularly from linear or branched, saturated or unsaturated $C_{11}$-$C_{21}$ alkyl and alkenyl radicals.

Preferably, x and z, which may be identical or different, are 0 or 1.

Advantageously, y is equal to 1.

Preferably, r, s and t, which may be identical or different, are 2 or 3, and even more particularly are equal to 2.

The anion is preferably a halide (chloride, bromide or iodide) or an alkyl sulfate, more particularly methyl sulfate. However, methanesulfonate, phosphate, nitrate, tosylate, an anion derived from an organic acid such as acetate or lactate, or any other anion that is compatible with the ammonium containing an ester function, may be used.

The anion $X^-$ is even more particularly chloride or methyl sulfate.

Among the ammonium salts of formula (XV), the compounds that are more particularly used are those in which:

$R_{22}$ denotes a methyl or ethyl radical,
x and y are equal to 1;
z is equal to 0 or 1;
r, s and t are equal to 2;
$R_{23}$ is chosen from:
the radical $$R_{26}-\overset{O}{\underset{}{\overset{\|}{C}}}-$$

methyl, ethyl or $C_{14}$-$C_{22}$ hydrocarbon-based radicals;
a hydrogen atom;
$R_{25}$ is chosen from:
the radical $$R_{28}-\overset{O}{\underset{}{\overset{\|}{C}}}-$$

a hydrogen atom;

$R_{24}$, $R_{26}$ and $R_{28}$, which may be identical or different, are chosen from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

Advantageously, the hydrocarbon-based radicals are linear.

Examples that may be mentioned include the compounds of formula (XV) such as the salts (especially chloride or methyl sulfate) of diacyloxyethyldimethylammonium, of diacyloxyethylhydroxyethylmethylammonium, of monoacyloxyethyldihydroxyethylmethylammonium, of triacyloxyethylmethylammonium or of monoacyloxyethylhydroxyethyldimethylammonium and mixtures thereof. The acyl radicals preferably contain 14 to 18 carbon atoms and are more particularly derived from a plant oil such as palm oil or sunflower oil. When the compound contains several acyl radicals, these radicals may be identical or different. Mention may be made in particular of distearoylethylhydroxyethylammonium methosulfate.

These products are obtained, for example, by direct esterification of triethanolamine, triisopropanolamine, an alkyldiethanolamine or an alkyl diisopropanolamine, which are optionally oxyalkylenated, with fatty acids or with mixtures of fatty acids of plant or animal origin, or by transesterification of the methyl esters thereof. This esterification is followed by quaternization using an alkylating agent such as an alkyl halide (preferably a methyl or ethyl halide), a dialkyl sulfate (preferably methyl or ethyl sulfate), methyl methanesulfonate, methyl para-toluenesulfonate, or glycol or glycerol chlorohydrin.

The composition used according to the invention may contain a mixture of mono-, di- and triester salts of quaternary ammonium with a weight majority of diester salts.

Examples of mixtures of ammonium salts that may be used include the mixture containing 15% to 30% by weight of acyloxyethyldihydroxyethylmethylammonium methyl sulfate, 45% to 60% diacyloxyethylhydroxyethylmethylammonium methyl sulfate and 15% to 30% triacyloxyethylmethylammonium methyl sulfate, the acyl radicals containing from 14 to 18 carbon atoms and being derived from optionally partially hydrogenated palm oil.

Ammonium salts containing at least one ester function, described in U.S. Pat. Nos. 4,874,554 and 4,137,180, may also be used.

As non-limiting examples of surfactants that are suitable for producing the compositions according to the invention, mention may be made of Rewopol SB F 12 P, the active agent of which is sodium lauryl sulfosuccinate, Texapon Z 95 P, the active agent of which is sodium lauryl sulfate, Genamin KDMP, the active agent of which is behenyltrimethylammonium chloride, Dehyquart F 75, the active agent of which is dicetearoylethylhydroxyethylmethylammonium methosulfate, and Tween 21, the active agent of which is sorbitan monolaurate containing 4 mol of ethylene oxide.

When they are present, the surfactant(s) generally represent from 0.1% to 10% by weight relative to the total weight of the composition.

The composition used according to the invention comprises a cosmetically acceptable medium.

This medium is preferably aqueous, i.e. it comprises either water alone, or water and one or more solvents, for instance ethanol, propylene glycol, butylene glycol, isopropanol, glycol ethers such as monopropylene, dipropylene or tripropylene glycol ($C_1$-$C_4$)alkyl ethers, monoethylene, diethylene or triethylene glycol, dipropylene glycol or diethylene glycol, and mixtures thereof.

The medium may also be anhydrous or essentially anhydrous.

The composition used according to the invention may also comprise any additive that may be used in the field of application under consideration.

It is preferably aqueous.

In particular, it may comprise fragrances, UV-screening agents, preserving agents, antioxidants, pH regulators, sequestrants, free-radical scavengers, moisturizers, reducing agents, conditioning agents other than silicones, polymers and the surfactants mentioned previously, such as fatty esters, and vitamins.

A subject of the invention is also a cosmetic composition comprising, in a cosmetically acceptable medium, one or more volatile linear alkanes and one or more nonionic associative polymers, the nonionic associative polymer(s) being chosen from:

(1) celluloses modified with groups comprising at least one fatty chain, (2) hydroxypropyl guars modified with groups comprising at least one fatty chain, (3) copolymers of $C_1$-$C_6$ alkyl acrylates or methacrylates and of amphiphilic monomers comprising at least one fatty chain, (4) copolymers of hydrophilic acrylates or methacrylates and of hydrophobic monomers comprising at least one fatty chain, (5) polyurethane polyethers comprising in their chain both hydrophilic blocks of polyoxyethylenated nature and hydrophobic blocks that are aliphatic chains alone and/or cycloaliphatic and/or aromatic chains, (6) polymers with an aminoplast ether backbone containing at least one fatty chain.

The cosmetically acceptable medium and the volatile linear alkane(s) of the composition according to the invention may be defined in the same manner as the cosmetically acceptable medium and the volatile linear alkane(s) defined previously as regards the use according to the invention. The nonionic associative polymer(s) of families (1) to (6) of the composition according to the invention may be defined in the same manner as the nonionic associative polymers of families (1) to (6) defined previously as regards the use according to the invention.

The invention is illustrated by the examples that follow.

Example 1

A rinse-out care composition according to the invention is prepared. The formulation is given in Table 1. The contents are expressed as grams of product in the given form per 100 g of composition.

TABLE 1

| | |
|---|---|
| Myristyl/cetyl/stearyl myristate/palmitate/stearate mixture | 1.5 |
| Polydimethylsiloxane | 1.5 |
| Crosslinked ethyltrimethylammonium methacrylate chloride homopolymer as an inverse emulsion at 50% in mineral oil (Salcare SC95 from Ciba) | 1 |
| Polyethylene glycol distearate (150 OE) | 0.3 |
| Candelilla wax | 2 |
| Pregelatinized hydroxypropyl corn distarch phosphate (Structure Zea) | 0.2 |
| n-Undecane/n-Tridecane according to Example 2 of WO 2008/155059 | 8.5 |
| Cetylstearyl alcohol (50/50 C16/C18) | 8 |
| Copolymer of SMDI/polyethylene glycol bearing alkyl (methyl/C18) end groups, at 15% in a maltodextrin/water matrix (Aculyn 46 from Röhm & Haas) | 3 |
| Deionized water | qs 100 |
| Preserving agents | qs |
| Fragrance | qs |

This composition is applied to heads.
Improved softness, smoothing and suppleness are obtained.

Example 2

A rinse-out care composition that may be used according to the invention is prepared. The formulation is given in Table 2. The contents are expressed as grams of product in the given form per 100 g of composition.

TABLE 2

| | |
|---|---|
| Myristyl/cetyl/stearyl myristate/palmitate/stearate mixture (Crodamol MS PA from Croda) | 1.5 |
| Polydimethylsiloxane (Belsil DM 300 000 from Wacker) | 1.5 |
| Crosslinked ethyltrimethylammonium methacrylate chloride homopolymer as an inverse emulsion at 50% in mineral oil (Salcare SC95 from Ciba) | 1 |
| Polyurethane-39 at 20% active material (Luvigel Star from BASF) | 2.2 |
| Polyethylene glycol distearate (150 OE) | 0.3 |

TABLE 2-continued

| | |
|---|---|
| Candelilla wax | 2 |
| Pregelatinized hydroxypropyl corn distarch phosphate (Structure Zea from National Starch) | 0.2 |
| n-Undecane/n-Tridecane according to Example 2 of WO 2008/155059 | 8.5 |
| Cetylstearyl alcohol (50/50 C16/C18) | 8 |
| Deionized water | qs 100 |
| Preserving agents | qs |
| Fragrance | qs |

This composition is applied to heads.

An improvement in the cosmetic performance qualities is observed on dried hair.

Example 3

A leave-in care composition that may be used according to the invention is prepared. The formulation is given in Table 4. The contents are expressed as grams of product in the given form per 100 g of composition.

TABLE 3

| | |
|---|---|
| n-Dodecane/n-tetradecane mixture (Vegelight 1214 from Biosynthis) | 2 |
| Cetylstearyl alcohol (50/50 C16/C18) | 1 |
| Copolymer of SMDI/polyethylene glycol bearing alkyl (methyl/C18) end groups, at 15% in a maltodextrin/water matrix (Aculyn 46) | 4 |
| Crosslinked ethyltrimethylammonium methacrylate chloride homopolymer as a 50% dispersion in a mixture of esters (Salcare SC96) | 1.3 |
| Deionized water | qs 100 |
| Preserving agents | qs |
| Fragrance | qs |

This composition is applied to heads. An improvement in the cosmetic performance qualities in terms of smoothing and sheen is observed.

Example 4

A leave-in care composition that may be used according to the invention is prepared. The formulation is given in Table 4. The contents are expressed as grams of product in the given form per 100 g of composition.

TABLE 4

| | |
|---|---|
| Polydimethylsiloxane (Belsil DM 300 000 from Wacker) | 2 |
| n-Dodecane (Vegelight 12 from Biosynthis) | 2 |
| Copolymer of SMDI/polyethylene glycol bearing alkyl (methyl/C18) end groups, at 15% in a maltodextrin/water matrix (Aculyn 46 from Röhm & Haas) | 2.5 |
| Crosslinked ethyltrimethylammonium methacrylate chloride homopolymer as a 50% dispersion in a mixture of esters (Salcare SC96 from Ciba) | 1 |
| Deionized water | qs 100 |
| Preserving agents | qs |
| Fragrance | qs |

This composition is applied to heads.

Improved cosmetic performance qualities in terms of softness, smoothing and suppleness are observed.

Example 5

A leave-in care composition that may be used according to the invention is prepared. The formulation is given in Table 5. The contents are expressed as grams of product in the given form per 100 g of composition.

TABLE 5

| | |
|---|---|
| Polydimethylsiloxane (Belsil DM 300 000) | 2 |
| n-Dodecane/n-tetradecane mixture (Vegelight 1214) | 2 |
| Crosslinked ethyltrimethylammonium methacrylate chloride homopolymer as a 50% dispersion in a mixture of esters (Salcare SC96) | 1 |
| Copolymer of SMDI/polyethylene glycol bearing alkyl (methyl/C18) end groups, at 15% in a maltodextrin/water matrix (Aculyn 46) | 2.5 |
| Deionized water | qs 100 |
| Preserving agents | qs |
| Fragrance | qs |

This composition is applied to heads.

Improved cosmetic performance qualities in terms of softness, smoothing and suppleness are observed, in particular on dried hair.

The above written description of the invention provides a manner and process of making and using it such that any person skilled in this art is enabled to make and use the same, this enablement being provided in particular for the subject matter of the appended claims, which make up a part of the original description.

As used herein, the words "a" and "an" and the like carry the meaning of "one or more."

The phrases "selected from the group consisting of," "chosen from," and the like include mixtures of the specified materials. Terms such as "contain(s)" and the like are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. In this regard, certain embodiments within the invention may not show every benefit of the invention, considered broadly.

The invention claimed is:

1. A method for conditioning keratin fibres, comprising application to said keratin fibers of a cosmetic composition comprising, in a cosmetically acceptable medium, at least two volatile linear alkanes comprising from 10 to 14 carbon atoms differing from each other by a carbon number n of at least 1, and one or more nonionic associative polymers selected from the group consisting of
  a cellulose modified with a group comprising at least one fatty chain; and
  a polyurethane polyether that is a triblock copolymer comprising in their chain both a hydrophilic block and a hydrophobic block, which may be an aliphatic sequence alone, a cycloaliphatic sequence, and/or an aromatic sequence, wherein the hydrophilic block is a polyoxyethylenated chain comprising 50 to 1000 oxyethylene groups.

2. The method according to claim 1, wherein the volatile linear alkanes(s) are of plant origin.

3. The method according to claim 1, wherein the at least two volatile linear alkanes are chosen from n-decane, n-undecane, n-dodecane, n-tridecane and n-tetradecane.

4. The method according to claim 1, wherein the at least two volatile linear alkanes(s) are chosen from n-undecane, n-dodecane, n-tridecane and n-tetradecane.

5. The method according to claim 4, wherein the at least two volatile linear alkanes are an n-undecane/n-tridecane mixture.

6. The method according to claim 1, wherein the at least two volatile linear alkanes(s) alkanes represent from 0.5% to 90% by weight of the total weight of the composition.

7. The method according to claim 1, wherein the nonionic associative polymer(s) represent from 0.05% to 10% by weight of the total weight of the composition.

8. The method according to claim 1, wherein the composition further comprises one or more non-silicone fatty substances.

9. The method according to claim 1, wherein the composition further comprises one or more silicones.

10. A composition comprising, in a cosmetically acceptable medium, at least two volatile linear alkanes comprising from 10 to 14 carbon atoms differing from each other by a carbon number n of at least 1, and one or more nonionic associative polymers, wherein the nonionic associative polymer(s) are selected from the group consisting of:

a cellulose modified with a group comprising at least one fatty chain; and a polyurethane polyether that is a triblock copolymer comprising in their chain both a hydrophilic block and a hydrophobic block, which may be an aliphatic sequence alone, a cycloaliphatic sequence, and/or an aromatic sequence, wherein the hydrophilic block is a polyoxyethylenated chain comprising 50 to 1000 oxyethylene groups.

* * * * *

UNITED STATES PATENT AND TRADEMARK OFFICE
CERTIFICATE OF CORRECTION

PATENT NO. : 9,566,220 B2
APPLICATION NO. : 14/683345
DATED : February 14, 2017
INVENTOR(S) : Patricia Desenne et al.

It is certified that error appears in the above-identified patent and that said Letters Patent is hereby corrected as shown below:

In the Claims

Column 31, Line 12:
"two volatile linear alkanes(s) alkanes represent from 0.5% to"
Should read:
--two volatile linear alkanes represent from 0.5% to--.

Signed and Sealed this
Seventh Day of November, 2017

Joseph Matal
*Performing the Functions and Duties of the*
*Under Secretary of Commerce for Intellectual Property and*
*Director of the United States Patent and Trademark Office*